US00PP14983P2

(12) United States Plant Patent
Heffner

(10) Patent No.: US PP14,983 P2
(45) Date of Patent: Jul. 6, 2004

(54) DOUBLE IMPATIENS PLANT NAMED 'BODDBLPCHFR'

(50) Latin Name: *Impatiens walleriana*
Varietal Denomination: Boddblpchfr

(75) Inventor: Michael R. Heffner, Santa Barbara, CA (US)

(73) Assignee: John Bodgers + Sons, Co., South El Monte, CA (US)

( * ) Notice: Subject to any disclaimer, the term of this patent is extended or adjusted under 35 U.S.C. 154(b) by 0 days.

(21) Appl. No.: 10/684,570

(22) Filed: Oct. 13, 2003

(51) Int. Cl.[7] ..... A01H 5/00
(52) U.S. Cl. ..... Plt./317
(58) Field of Search ..... Plt./317

*Primary Examiner*—Kent Bell
(74) *Attorney, Agent, or Firm*—C. A. Whealy

(57) ABSTRACT

A new and distinct cultivar of Double Impatiens plant named 'Boddblpchfr', characterized by its compact, mounded and outwardly spreading plant habit; freely basal branching habit; dark green leaves; large pink-colored flowers; fully double flower form; freely flowering habit; and flowers positioned above and beyond the foliage.

1 Drawing Sheet

Botanical classification: *Impatiens walleriana* cultivar Boddblpchfr.

BACKGROUND OF THE INVENTION

The present Invention relates to a new and distinct cultivar of Double Impatiens plant, botanically known as *Impatiens walleriana,* and hereinafter referred to by the name 'Boddblpchfr'.

The new Impatiens is a product of a planned breeding program conducted by the Inventor in Lompoc, Calif. The objective of the breeding program was to develop new compact Double Impatiens cultivars with large fully double flowers, excellent branching, and attractive flower and foliage colors.

The new Impatiens originated from a cross made by the Inventor in September, 1999, of a proprietary *Impatiens walleriana* selection identified as 9IM1500-2, not patented, as the female, or seed parent, with a proprietary *Impatiens walleriana* selection identified as 9IM1784-5, not patented, as the male, or pollen parent. The cultivar Boddblpchfr was discovered and selected by the Inventor as a flowering plant within the progeny of the stated cross in a controlled environment in Lompoc, Calif.

Asexual reproduction of the new cultivar by terminal cuttings taken at Lompoc, Calif. since 1999, has shown that the unique features of this new Impatiens are stable and reproduced true to type in successive generations of asexual reproduction.

SUMMARY OF THE INVENTION

The following traits have been repeatedly observed and are determined to be the unique characteristics of 'Boddblpchfr'. These characteristics in combination distinguish 'Boddblpchfr' as a new and distinct cultivar:

1. Compact, mounded and outwardly spreading plant habit.
2. Freely basal branching habit.
3. Dark green leaves; densely foliated.
4. Large pink-colored flowers.
5. Fully double flower form.

6. Freely flowering habit.
7. Flowers positioned above and beyond the foliage.

Plants of the new Impatiens differ from plants of the female parent in flower form and coloration as flowers of plants of the female parent are semi-double in form and have white-colored petals. Plants of the new Impatiens differ from plants of the male parent in flower form and coloration as flowers of plants of the male parent are single and have red-colored petals.

Plants of the new Impatiens can be compared to plants of the Impatiens cultivar Boddblbrp, disclosed in U.S. Plant patent application Ser. No. 10/684,573. Plants of the new Impatiens differ primarily from plants of the cultivar Boddblbrp in flower coloration.

The new Impatiens can also be compared to the *Impatiens walleriana* cultivar Pink Ruffle, disclosed in U.S. Plant Pat. No. 9,616. However, in side-by-side comparisons conducted in Lompoc, Calif., plants of the new Impatiens differed from plants of the cultivar Pink Ruffle in the following characteristics:

1. Plants of the new Impatiens were more compact, were not as vigorous, had shorter internodes and were denser than plants of the cultivar Pink Ruffle.
2. Plants of the new Impatiens were more freely branching than plants of the cultivar Pink Ruffle.
3. Plants of the new Impatiens had broader leaves than plants of the cultivar Pink Ruffle.
4. Plants of the new Impatiens were more freely flowering than plants of the cultivar Pink Ruffle.
5. Plants of the new Impatiens had smaller flowers than plants of the cultivar Pink Ruffle.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph at the top of sheet comprises a side perspective view of a typical flowering plant of 'Boddblpchfr' grown in a 15-cm container for about 12 weeks.

The photograph at the bottom of the sheet comprises a close-up view of typical developing flowers and leaves of 'Boddblpchfr'.

DETAILED BOTANICAL DESCRIPTION

The cultivar Boddblpchfr has not been observed under all possible environmental conditions. The phenotype may vary somewhat with variations in environment such as temperature and light intensity without, however, any variance in genotype. Plants used in the aforementioned photographs and for the following description were grown in Lompoc, Calif., under commercial practice during the winter and early spring in a polycarbonate-covered greenhouse with day temperatures about 18 to 24° C., night temperatures about 16 to 18° C. and light levels about 4,000 to 8,000 foot-candles. Unrooted cuttings were directly planted in 15-cm containers and grown for about 12 weeks. In the following description, color references are made to The Royal Horticultural Society Colour Chart, 1995 Edition, except where general terms of ordinary dictionary significance are used.

Botanical classification: *Impatiens walleriana* cultivar Boddblpchfr.

Parentage:

*Female parent.*—Proprietary *Impatiens walleriana* selection identified as 9IM1500-2, not patented.

*Male parent.*—Proprietary *Impatiens walleriana* selection identified as 9IM1784-5, not patented.

Propagation:

*Type cutting.*—Terminal cuttings.

*Time to initiate roots.*—About 10 to 14 days at 21° C.

*Time to produce a rooted cutting or liner.*—About 21 to 28 days at 21° C.

*Root description.*—Numerous and fine.

*Rooting habit.*—Freely branching.

Plant description:

*General appearance.*—Compact, mounded and outwardly spreading. Appropriate for 15-cm and larger containers.

*Growth and branching habit.*—Moderately vigorous and freely-basal branching with about 15 lateral branches developing at the base; dense and bushy growth. Pinching, that is, removal of the terminal apices, will enhance branching.

*Crop time.*—About eight to nine weeks are required to produce a finished flowering plant from planting an unrooted cutting in a 15-cm pot.

*Plant height.*—About 14 cm.

*Plant diameter or spread.*—About 36.5 cm.

*Lateral branches.*—Length: About 20 cm. Diameter: About 6 mm. Internode length: About 4 cm. Texture: Smooth. Color: 146D.

*Foliage description.*—Arrangement: Simple, alternate. Length: About 5.25 cm. Width: About 4.3 cm. Shape: Elliptic. Apex: Acute. Base: Attenuate. Margin: Serrate, rounded. Texture, upper and lower surfaces: Glabrous, smooth. Venation pattern: Pinnate, arcuate. Color: Developing and fully expanded foliage, upper surface: 147A. Developing and fully expanded foliage, lower surface: 147B. Venation, upper and lower surfaces: 147C. Petiole: Length: About 2 cm. Diameter: About 3 mm. Color: 147C.

Flower description:

*Flower type and habit.*—Numerous and consistently large fully double flowers. Freely and continuously flowering. Flower buds open similar to a rose in fullness; flowers rounded. Flowers arise from leaf axils. Typically about 35 flowers and flower buds per lateral branch. Flowers positioned above and beyond the foliage and typically face mostly outward. Flowers last about five to seven days under greenhouse conditions. Flowers not persistent. Flowers not fragrant.

*Flowering season.*—Year-round under greenhouse conditions. In the garden, flowering is continuous from spring until fall.

*Flower size.*—Diameter: About 3.7 cm. Depth: About 2.3 cm.

*Flower buds.*—Length, at stage of showing color: About 1.8 cm. Diameter, at stage of showing color: About 9 mm. Shape: Ovoid. Color: 55D.

*Petals.*—Quantity/arrangement: About 32 per flower; imbricate. Length, outer petals: About 2.6 cm. Width, outer petals: About 2.8 cm. Shape: Oval to cordate. Apex: Emarginate. Base: Acute. Margin: Entire. Texture, upper and lower surfaces: Velvety, smooth. Color: When opening, upper surface: 55A. When opening, lower surface: 55C to 55D. Fully opened, upper surface: 55B; towards the base, 53D; color becoming closer to 55C to 55D with development. Fully opened, lower surface: 56B to 56C; towards the margins, 55C.

*Spurs.*—Length: About 2.8 cm. Color: 146C.

*Sepals*—Quantity/arrangement: Five in a single whorl. Calyx length: About 1.1 cm. Calyx diameter: About 9 mm. Shape: Elliptic. Apex: Broadly acute. Margin: Entire. Texture, upper and lower surfaces: Smooth. Color: Upper surface: 145D. Lower surface: 145C.

*Peduncles.*—Length: About 4.8 cm. Diameter: About 1.5 mm. Angle: About 45° to the lateral branch. Strength: Moderately strong. Color: 145A.

*Reproductive organs.*—None observed.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of Double Impatiens plant named 'Boddblpchfr', as illustrated and described.

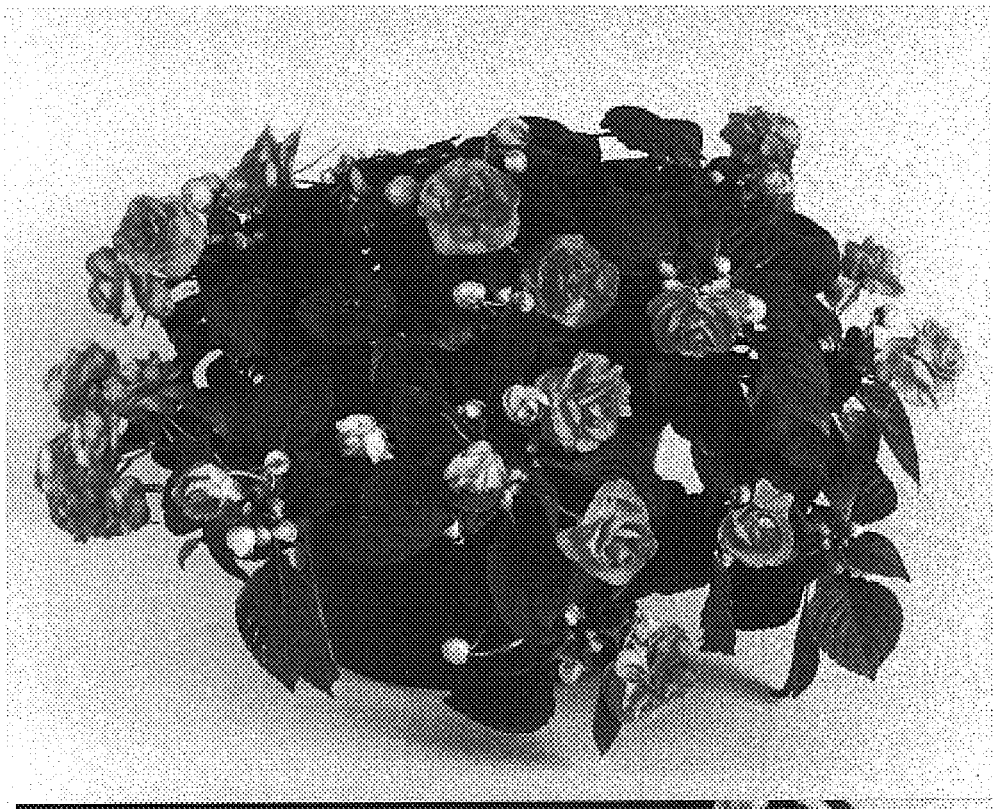
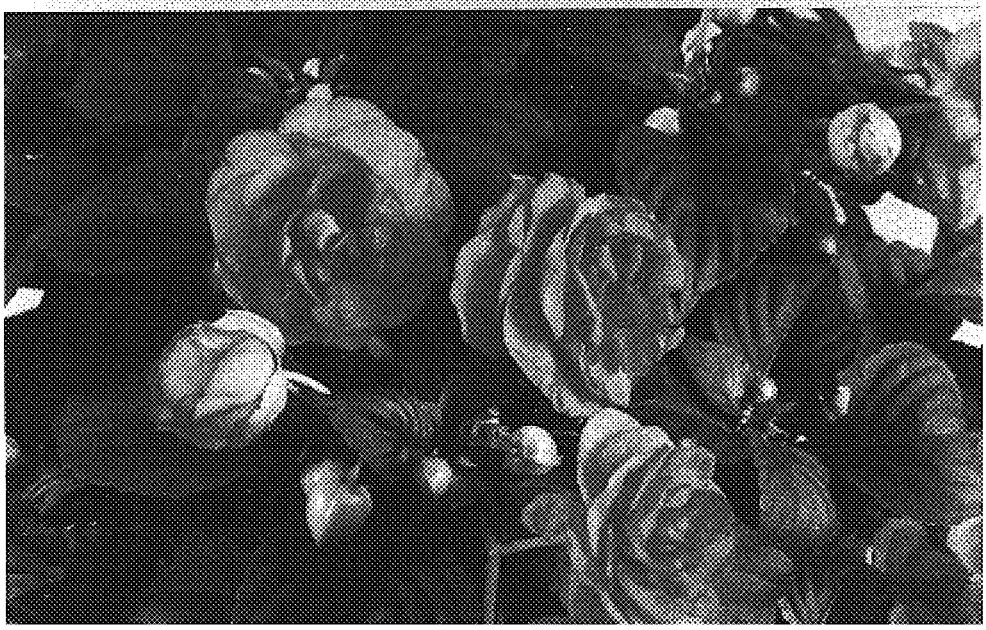

* * * * *